(12) United States Patent
Paul et al.

(10) Patent No.: US 12,239,804 B2
(45) Date of Patent: Mar. 4, 2025

(54) UMBILICAL ARTERIAL CATHETERIZATION DEVICE

(71) Applicant: Christiana Care Health System, Inc., Wilmington, DE (US)

(72) Inventors: David Paul, Wilmington, DE (US); Pedro Urday, Mt. Laurel, NJ (US); Mary Lemma, West Chester, PA (US); Ally McCabe, York, PA (US); Nathan Patel, Newark, DE (US); Sienna Pyle, Philadelphia, PA (US); Joseph Michael Korn, Laurel Springs, NJ (US); Rachael Nicole Passantino, Nyack, NY (US); Sarah Anne Geissler, Colts Neck, NJ (US); Zankar Mihir Modi, Hockessin, DE (US)

(73) Assignee: CHRISTIANA CARE HEALTH SYSTEM, INC., Wilmington, DE (US)

( * ) Notice: Subject to any disclaimer, the term of this patent is extended or adjusted under 35 U.S.C. 154(b) by 0 days.

(21) Appl. No.: 18/035,040

(22) PCT Filed: Nov. 15, 2021

(86) PCT No.: PCT/US2021/059364
§ 371 (c)(1),
(2) Date: May 2, 2023

(87) PCT Pub. No.: WO2022/104198
PCT Pub. Date: May 19, 2022

(65) Prior Publication Data
US 2023/0381458 A1  Nov. 30, 2023

Related U.S. Application Data

(60) Provisional application No. 63/114,176, filed on Nov. 16, 2020.

(51) Int. Cl.
*A61M 25/02* (2006.01)
*A61B 17/02* (2006.01)
*A61B 90/30* (2016.01)

(52) U.S. Cl.
CPC ......... *A61M 25/02* (2013.01); *A61B 17/0293* (2013.01); *A61B 90/30* (2016.02);
(Continued)

(58) Field of Classification Search
CPC .......... A61M 25/02; A61M 2025/0213; A61M 2025/024; A61M 2025/0253;
(Continued)

(56) References Cited

U.S. PATENT DOCUMENTS

| 8,753,355 B2 | 6/2014 | Bachmann |
| 2003/0036733 A1 | 2/2003 | Martin |

(Continued)

FOREIGN PATENT DOCUMENTS

CN  211272857  8/2020

OTHER PUBLICATIONS

Francisco Javier Guzmán-de la Garza, et al., Ultrasound-guided umbilical venous catheterisation: A cost-effectiveness analysis, Anales de Pediatría (English Edition), vol. 92, Issue 4, 2020, pp. 215-221, ISSN 2341-2879, https://doi.org/10.1016/j.anpede.2019.04.013.
(Continued)

*Primary Examiner* — Ahmed M Farah
(74) *Attorney, Agent, or Firm* — FisherBroyles LLP

(57) ABSTRACT

An umbilical arterial catherization device comprising a brace and a dilator. The brace has a body for supporting and stabilizing an umbilical cord end. The body may have resilient foam for grasping the umbilical cord, and may include a strap operable to secure part of the body to itself, after being wrapped around the umbilical cord. The dilator has a hook for engaging an open end of an arterial lumen,
(Continued)

and a catch operable to fix the dilator to the brace in a position for dilating the arterial lumen. Both hands may be used to place the dilator while the device serves to stabilize and support the umbilical cord without use of the hands. The device may include a lighting element for illuminating the end of the umbilical cord to aid in visualization of the arterial lumen and facilitate proper placement of the catch within the arterial lumen.

18 Claims, 3 Drawing Sheets

(52) U.S. Cl.
CPC .................. *A61B 2090/309* (2016.02); *A61M 2025/0213* (2013.01); *A61M 2025/026* (2013.01); *A61M 2025/028* (2013.01); *A61M 2205/586* (2013.01)

(58) Field of Classification Search
CPC .... A61M 2025/026; A61M 2025/0266; A61M 2025/028; A61M 2025/0286; A61B 90/30; A61B 2090/309
USPC .............................................................. 606/1
See application file for complete search history.

(56) References Cited

U.S. PATENT DOCUMENTS

| | | | |
|---|---|---|---|
| 2003/0125668 A1* | 7/2003 | Bierman | A61M 25/02 604/174 |
| 2004/0215211 A1 | 10/2004 | Watson | |
| 2009/0105656 A1 | 4/2009 | Schaeffer | |
| 2010/0204699 A1* | 8/2010 | Wei | A61F 2/30 606/76 |
| 2011/0282290 A1 | 11/2011 | Kennard | |
| 2012/0232356 A1* | 9/2012 | Coelho | A61B 5/0205 600/301 |
| 2014/0221735 A1* | 8/2014 | Californiaa | C12M 21/06 600/34 |
| 2016/0135844 A1* | 5/2016 | Chinchoy | A61B 5/4356 606/124 |
| 2016/0228252 A1* | 8/2016 | Keidar | A61F 2/2409 |
| 2017/0128101 A1* | 5/2017 | Patrinicola | A61B 17/7052 |
| 2018/0085249 A1* | 3/2018 | Carrasco | A61B 46/20 |
| 2018/0318554 A1* | 11/2018 | Karim | A61M 25/02 |
| 2020/0023165 A1 | 1/2020 | Dambkowski | |
| 2021/0338270 A1* | 11/2021 | Flake | A61B 17/3417 |

OTHER PUBLICATIONS

Guimarães AF, Souza AA, Bouzada MC, Meira ZM. Accuracy of chest radiography for positioning of the umbilical venous catheter. J Pediatr (Rio J). 2017;93:172-8.

International Search Report mailed Jan. 31, 2022 in International Application No. PCT/US2021/059364.

Kumar, P., Kumar, C., Nayak, M. et al. Umbilical arterial catheter insertion length: in quest of a universal formula. J Perinatol 32, 604-607 (2012).

Matthew B. Wallenstein, Gary M. Shaw, Wei Yang & David K. Stevenson (2019) Failed umbilical artery catheterization and adverse outcomes in extremely low birth weight infants, The Journal of Maternal-Fetal & Neonatal Medicine, 32:21, 3566-3570, DOI: 10.1080/14767058.2018.1468430.

McAdams RM, Winter VT, McCurnin DC, Coalson JJ. Complications of umbilical artery catheterization in a model of extreme prematurity. J Perinatol. 2009;29(10):685-692. doi:10.1038/jp.2009.73.

Philip AG. The evolution of neonatology. Pediatr Res. Oct. 2005;58(4):799-815. doi: 10.1203/01.PDR.0000151693.46655.66. Epub Feb. 17, 2005. PMID: 15718376.

Written Opinion of the International Searching Authority mailed Jan. 31, 2022 in International Application No. PCT/US2021/059364.

* cited by examiner

UMBILICAL ARTERIAL CATHETERIZATION DEVICE

CROSS-REFERENCE TO RELATED APPLICATION

This application claims the benefit of priority, under 35 USC 119(e), of U.S. Provisional Patent Application No. 63/114,176, filed Nov. 16, 2020, the entire disclosure of which is hereby incorporated herein by reference.

FIELD OF THE INVENTION

The present invention relates generally to a device for use in medical procedures to stabilize and support, and facilitate arterial catherization of, an umbilical cord, as may be needed for neonatological purposes and/or procedures.

DISCUSSION OF RELATED ART

In humans (and animals), the umbilical cord interconnects the fetus' circulatory system with the placenta, and acts to deliver nutrients such as oxygen, glucose and protein via the umbilical cord. Shortly after birth, the umbilical cord is typically clamped and cut, ultimately leaving the baby with an umbilical stump.

It is sometimes desirable to catheterize an artery of the umbilical cord for treatment of the baby. By way of example, umbilical arterial catheterization may be used to allow for easier sampling of the baby's blood, for continuous blood pressure monitoring, for administration of medications and/or fluids, and/or for monitoring of arterial gas pressure. It has been estimated that about two percent of the babies born in the United States require an umbilical arterial catheterization.

Performing the arterial catheterization can be challenging for several reasons. First, the umbilical cord itself is relatively flaccid and difficult to stabilize. Often, one hand of the physician is devoted to stabilizing the umbilical cord, leaving only one had to perform the catherization, which is difficult. Second, the arterial lumen is quite small, often approximately 1 mm or less in diameter or crosswise dimension. Accordingly, even when using both hands, with assistance of another person to stabilize the umbilical cord, it is difficult to properly identify the arterial lumen and to properly place the catheter in the arterial lumen. Thus, attempts at catherization are difficult and often time-consuming. It has been estimated that approximately 11% to 38% of umbilical arterial catheterization attempts are unsuccessful. If the attempt is unsuccessful, one or more subsequent attempts are required, which is further time-consuming. Delays in successful catherization can result in and/or contribute to increased utilization of high-skilled staff, increased time consumption in an acute unit, a lack of central access to better monitor acutely ill infants, increased risk for arterial perforation with increased attempts, and overall decreased survival rates with failed catheterizations, all of which are undesirable.

What is needed is a device that facilitates umbilical arterial catheterization, to increase the catheterization success rate and save time, allowing doctors and facilities to meet the needs of more patients, and increase infant survival rates.

SUMMARY

The present invention provides an umbilical arterial catherization device that facilitates umbilical arterial catheterization, to increase the catheterization success rate and save time, allowing doctors and facilities to meet the needs of more patients, and increase infant survival rates. The device comprises a brace having a body adapted to support and stabilize the cut end of an umbilical cord. The device further comprises a dilator having a hook having a tip dimensioned for receipt within a lumen of an artery of the umbilical cord, and a catch joined to said hook and operable to fix said dilator in a desired position relative to said brace to maintain the artery in a dilated position. Optionally, the device may further include a lighting element operable to provide illumination to a free end of an umbilical cord, when supported in the device, to aid in the visualization of the arterial lumen and thus facilitate proper placement of the catch within the arterial lumen.

BRIEF DESCRIPTION OF THE FIGURES

An understanding of the following description will be facilitated by reference to the attached drawings, in which.

DETAILED DESCRIPTION

The present invention relates to an umbilical arterial catheterization device that facilitates umbilical arterial catheterization, to increase the catheterization success rate and increase the efficiency of utilization of neonatological medical staff and medical facilities. By way of non-limiting illustrative example, an exemplary umbilical arterial catheterization device in accordance with the present invention is discussed below with reference to the exemplary embodiment shown in FIGS. 1-9.

The umbilical arterial catheterization device 100 has two principal components, which in this exemplary illustrative embodiment, namely, a brace 40 and a dilator 80. In this exemplary embodiment, these components are formed as two discrete components. However, in other embodiments, these components may be incorporated into a greater or lesser number of components.

Figure 1:
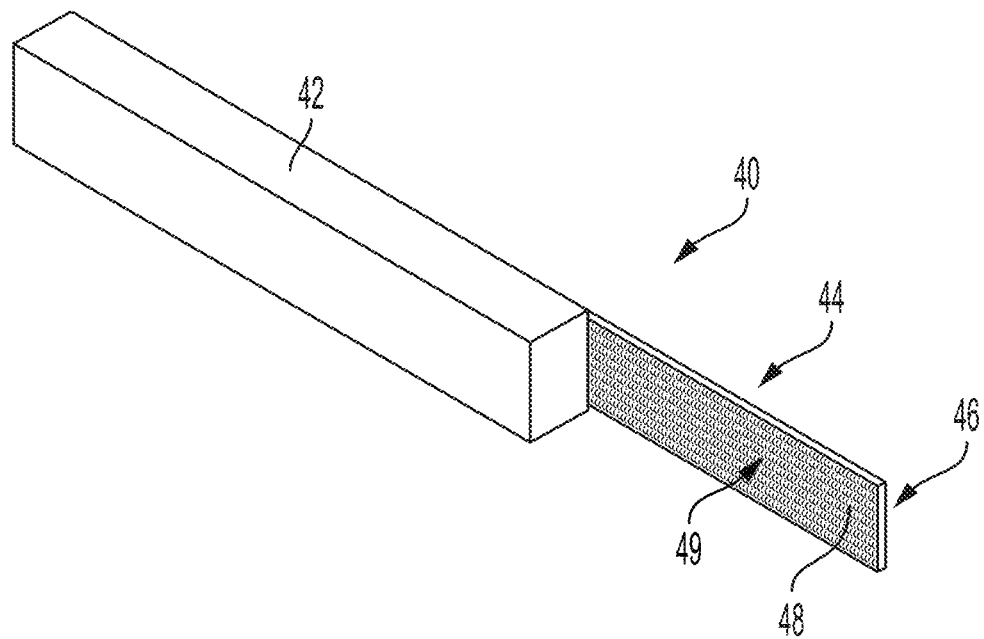
FIG. 1 is a perspective view of an exemplary brace of an umbilical arterial catheterization device in accordance with an exemplary embodiment of the present invention.

Referring now to FIG. 1, a brace 40 in accordance with an exemplary embodiment of the present invention is shown. The brace 40 serves to engage and stabilize a portion of the umbilical cord. Without support and stabilization the umbilical cord tends to be flaccid and unstable. As will be appreciated from FIG. 1, this exemplary brace 40 includes a longitudinally elongated body 42 of resilient material for abutting and supporting the umbilical cord, and a fastener 44 for securing/fixing the body 42 in an operative position in which the brace is stability and supporting the umbilical cord. In this exemplary embodiment, the body 42 is constructed of a resilient medical grade polyurethane foam (e.g., foam having a density of approximately 0.03 g/cm 3). Accordingly, the body 42 can be wrapped firmly around the umbilical cord and the foam will deform, place pressure upon, and ultimately create friction supporting the umbilical cord. Any suitable material and structure may be used for the stabilizing brace, as will be appreciated by those skilled in the art.

The fastener 44 is structured to allow for securing/fixing the body 42 in the desired position relative to the umbilical cord. In this embodiment, the fastener 44 is provided as a longitudinally elongated strap 48, which may be fixed to, releasably mountable to, or separate from, the body 42. In certain embodiments, the fastener 44 includes one or more fields of hook-type and/or loop-type fasteners of a hook-and-loop fastener system. In a preferred embodiment, the fastener 44 is provided as a strap having a first continuous field of hook-type (or loop-type) fasteners on one side (e.g., to mate with complementary loop-type (or hook-type) fasteners on the body 42), and having a second continuous field of complementary loop-type (or hook-type) fasteners on its opposite side. In this manner, the fastener 44 may be fixed to the body 42, and the body 42 and fastener 44 may be collectively wrapped around the umbilical cord and the fastener 44 may be secured to itself in a range of longitudinal positions (to accommodate umbilical cords of different sizes) to secure/fix the body 42/brace 40 in the desired position relative to the umbilical cord. Additionally, this configuration leaves a field of hook-and-loop type fasteners exposed on an outer surface of the fastener 44, which is advantageous for reasons discussed below. It will be appreciated by those skilled in the art that the fastener may have any suitable structure.

Preferably, the umbilical cord is pulled taut and the brace 40 is fastened to the cord in abutting relationship to the baby's abdomen, so that the body 42 provides an upwardly-acting friction force that serves to support and stabilize the umbilical cord.

Figure 2:
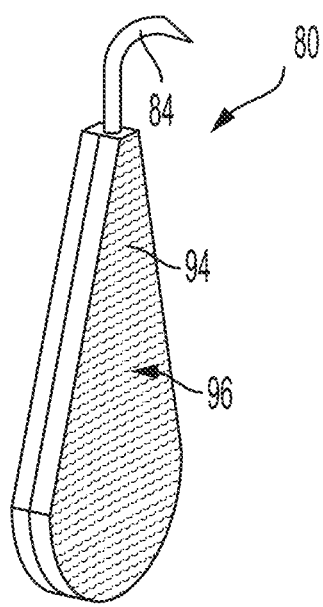
FIG. 2 is a perspective view of an exemplary dilator of an umbilical arterial catheterization device in accordance with an exemplary embodiment of the present invention.
Figure 3:
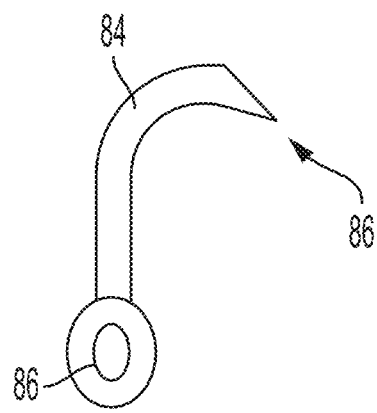
FIG. 3 is a side view of an exemplary hook of the dilator of FIG. 2.
Figure 4:
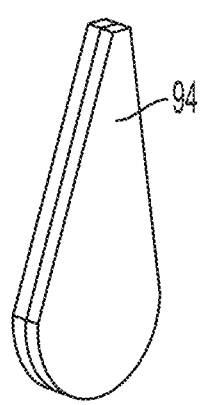
FIG. 4 is a perspective view of an exemplary catch of the dilator of FIG. 2.

FIG. 2 is a perspective view of a dilator 80 of an umbilical arterial catheterization device 100 in accordance with an exemplary embodiment of the present invention. The dilator 80 serves to dilate the arterial lumen, and to retain the arterial lumen in a dilated configuration, preferably without requiring manual assistance from medical personnel. Accordingly, with use of the dilator 80, both of a neonatologist's hands may be devoted to placement of the umbilical arterial catheter within the arterial lumen. As will be appreciated by reference to FIGS. 2-4, this exemplary dilator 80 includes a hook 84 and a catch 94. In this exemplary embodiment, the hook 84 is constructed of stainless steel, includes a sharp point 86 at one end, for engaging umbilical cord tissue to dilate the arterial lumen, and includes a loop 86 at its opposite end, which serves as a mounting point for attachment of the catch 94, e.g. by stitching or fastener, as will be appreciated from FIGS. 3 and 4.

The catch 94, when attached to the hook 84 as shown in FIG. 2, acts as a manually-graspable handle by which neonatologist may support and manipulate the hook 84 to engage umbilical cord tissue and dilate the arterial lumen.

The catch 94 further includes a fastener for securing the catch 94 to the brace 40 after the arterial lumen has been dilated, so that the arterial lumen may be maintained in the dilated configuration by the umbilical arterial catheterization device 100.

The catch 94 includes a field of fastener 96 of a hook-and-loop fastener system, preferably of a type complementary to the fastener 46 exposed on the outer surface of the fastener 44 of the brace 40, in this exemplary embodiment, a field of loop-type fastener.

Figure 5:
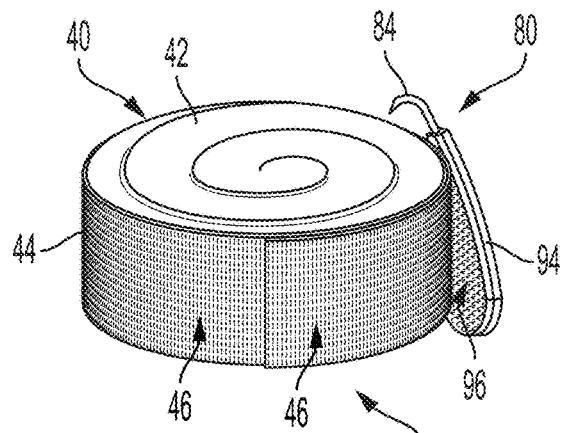
FIG. 5 is a perspective view of the umbilical arterial catheterization device in an operative configuration, with the dilator of FIG. 2 mounted to the brace of FIG. 1.

FIG. 5 is a perspective view showing the umbilical arterial catheterization device 100 in an operative configuration, with fastener 44 of the brace 40 wrapped around the body 42 and secured to itself, and loop-type fastener 96 on one side the catch 94 of the dilator 80 secured to hook-type fastener 46 on the exposed outer surface of the fastener 44 of the brace 40.

Figure 6:
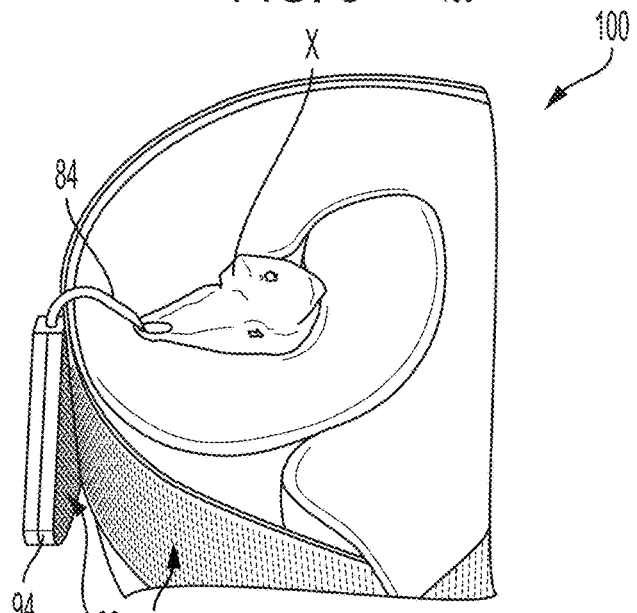
FIG. 6 is a perspective view of the umbilical arterial catheterization device of FIG. 5 in use to dilate an umbilical artery.

In use, the umbilical arterial catheterization device 100 can be positioned with the body 42 of the brace 40 wrapped tightly around an umbilical cord X, such that the body 42 engages and embraces the umbilical cord, as shown in FIG. 6. Preferably, the umbilical cord X is pulled taut before the brace 40 is fastened to the cord in abutting relationship to the baby's abdomen. The fastener 44 of the brace 40 may then be pulled taut as it is wrapped around the body 42, and a free end of the fastener 44 may be secured to itself, e.g., be engaging loop-type fastener on an inner surface of the fastener 44 with complementary hook-type fastener on an outer surface of the fastener 44, as shown in FIG. 6. In this manner, the body 42 provides an upwardly-acting friction force that serves to support and stabilize the umbilical cord. Optionally, the umbilical cord may be trimmed at an upper surface of the device 100, as shown in FIG. 6. In this manner, the free/cut end of the umbilical cord X is exposed at the upper edge of the device 100, and the cord is supported and stabilized by the brace 40.

Next, the physician/user may visualize an artery of the umbilical cord X. This may be challenging, since the artery may have a small lumen (e.g., approx. 1 mm or less in diameter or crosswise dimension) in a relaxed state, and further the artery may present in a closed state, with a diameter or crosswise dimension of approximately 0 mm), since the artery is surrounded by smooth muscle tissue that may contract when the cord is cut.

The physician/user may then manually grasp the catch 94, and manipulate the catch 94 to cause the point/tip 86 of the hook 84 to enter the arterial lumen and engage umbilical cord tissue. The physician/user may then pull the catch 94 laterally, to apply traction in a direction transverse to a direction of elongation of the artery, to stretch/open/dilate the open end of the artery. The physician/user may then press the catch 94 against the outer surface of the brace 40 to cause the catch's fastener 96 to engage the brace 40, e.g., to cause loop type fastener 96 on the catch 94 of the dilator 80 to engage hook-type fastener 46 on an outer surface of the fastener 44 of the brace 40. This fastens the dilator 80 to the brace 40, such that the physician/user may release his/her grasp of the catch 94, and have the umbilical arterial catheterization device 100 maintain the arterial lumen in the stretched/opened/dilated state, thereby freeing both of the physician/user's hands for other tasks. By way of example, the arterial lumen may be dilated to have a diameter/crosswise dimension of approximately 3.5 mm, in view of typical suitable catheters having diameters ranging in size from approx. 1.2 to approx. 1.7 mm in outer diameter. FIG. 6 shows the device 100 in an operative state, holding open the arterial artery of the umbilical cord X.

Figure 7:
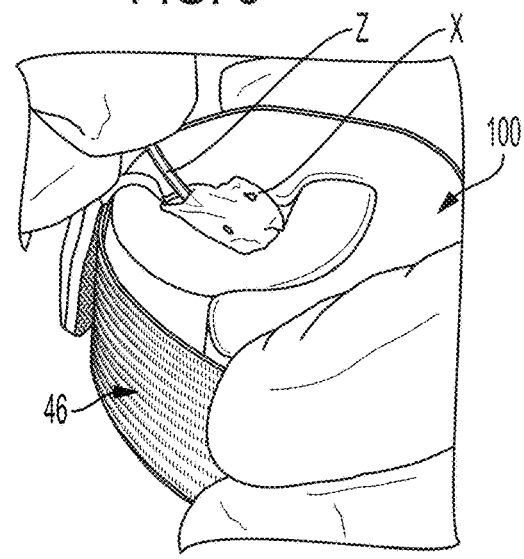
FIG. 7 is a perspective view of the umbilical arterial catheterization device of FIG. 5 showing placement of a catheter within the dilated umbilical artery.

The physician/user may then use both hands to advance a catheter Z into the dilated end of the umbilical artery. FIG. 7 shows successful placement of catheter Z within the lumen of the umbilical artery of umbilical cord X supported by the umbilical arterial catheterization device 100.

After suitable placement of the catheter Z, the catch 94/dilator 80 may be decoupled from the brace 40, and the fastener 44 of the brace may be decoupled to permit removal of the brace 40 from engagement with the umbilical cord.

Figure 8:
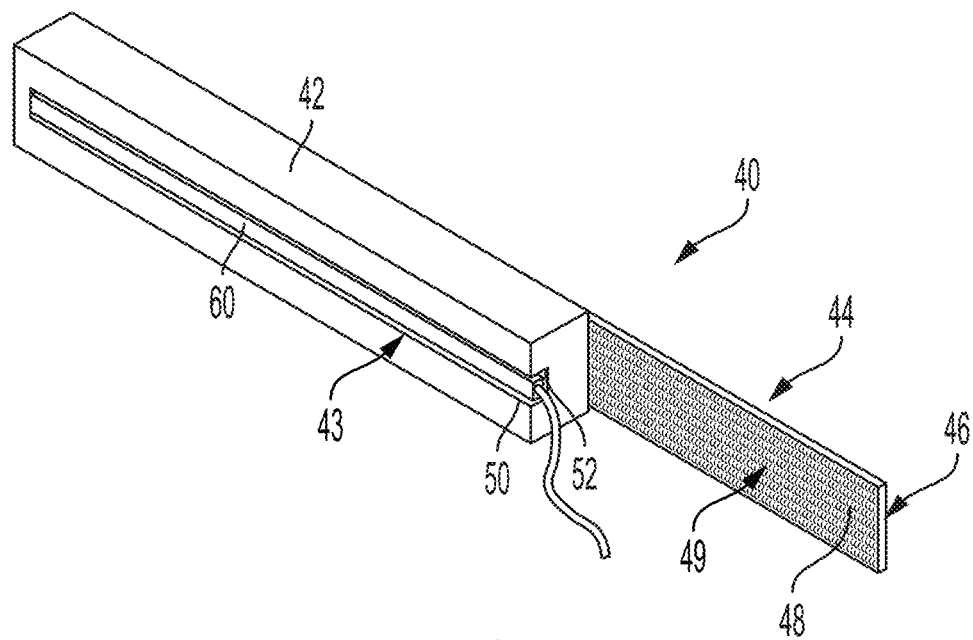
FIG. 8 is an exemplary brace of an umbilical arterial catheterization device in accordance with an alternative embodiment of the present invention.

Referring now to FIG. 8, a brace 40 in accordance with an alternative embodiment of the present invention is shown. The brace 40 is similar to that shown in FIG. 1, but further includes a lighting element for providing illumination to an umbilical cord captured by the brace. The lighting element provides vessel illumination to aid the physician/user in better distinguishing the position and location of the artery and/or vein within the Wharton's jelly of the umbilical cord. The lighting element may be supported on the brace in any suitable manner.

The lighting element may have any suitable configuration. In one embodiment, the lighting element may comprise one or more light sources, such as LEDs. The light sources may be operatively connected, e.g., via a wire, to a power source that may be remotely located from the device. By way of alternative example, on another embodiment, the lighting element may comprise a light pipe for transmitting light emitted from a light source. In this embodiment, the light pipe/lighting source is operatively connected to an LED or other suitable light source, which may be located remotely from the device.

In this exemplary embodiment, the body 42 of the brace 40 is provided with a recess 50 open to a surface 43 of the body 42/inner surface of the brace 40 when in an operative position. The recess 50 is sized and shaped to receive the desired lighting element. In the exemplary embodiment shown, the recess 50 is provided as a longitudinally-extending channel 52 for receiving a longitudinally-extending lighting element 60, such as a light pipe operatively connected to an LED or other suitable light source.

Figure 9:
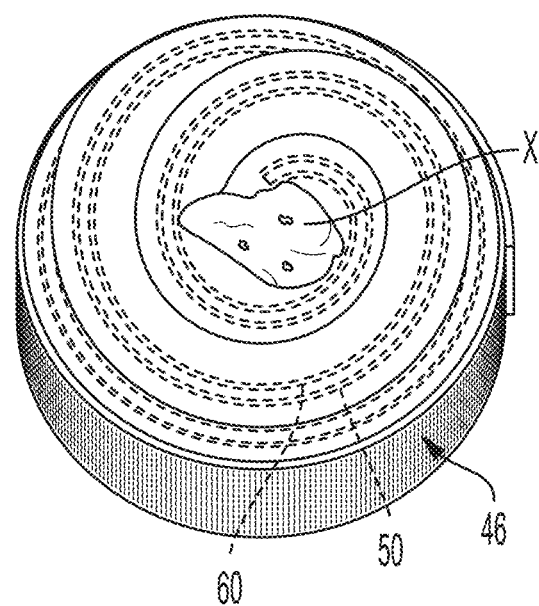
FIG. 9 is a perspective view of an alternative embodiment umbilical arterial catheterization device in an operative configuration, with the dilator of FIG. 2 mounted to the brace of FIG. 8.

As will be appreciated from FIG. 9, the brace 40 of this embodiment may be used in a manner similar to that described above with respect to FIGS. 1-7. In this embodiment, however, when the brace 40 is in an operative position and supporting an umbilical cord, light emitted from the lighting element 60 serves to light the upper portion (likely protruding from the brace 40) of the umbilical cord from below, which can assist the physician/user in visually identifying the arterial lumen, and in manipulating the catch 94 to cause the point/tip 86 of the hook 84 to enter the arterial lumen and engage the umbilical cord tissue, as will be best appreciated from FIG. 9.

While there have been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

What is claimed is:

1. An umbilical arterial catheterization device configured for catheterization of an artery of a human's umbilical cord, the umbilical arterial catheterization device comprising:
    a brace comprising a body adapted to support and stabilize a free end of the umbilical cord; and
    a dilator comprising:
        a hook having a tip dimensioned for receipt within the artery of the umbilical cord; and
        a catch joined to said hook and operable to fix said dilator to said brace;
    whereby said hook of said catch may be positioned within a lumen of the artery of the umbilical cord to dilate said artery while said brace is supporting and stabilizing the free end of the umbilical cord, and said catch may be secured to said brace in a desired position relative to said brace to maintain the artery in a dilated position.

2. The umbilical arterial catheterization device of claim 1, wherein said body of said brace is elongated longitudinally.

3. The umbilical arterial catheterization device of claim 1, wherein said brace is constructed of resilient foam.

4. The umbilical arterial catheterization device of claim 1, wherein said brace comprises a fastener operable to secure the body in an operative position for stably supporting an umbilical cord.

5. The umbilical arterial catheterization device of claim 4, wherein said fastener is operable to secure the body in an operative position for stably supporting an umbilical cord.

6. The umbilical arterial catheterization device of claim 4, wherein said fastener comprises an elongated strap.

7. The umbilical arterial catheterization device of claim 6, wherein said strap is integrally fixed to said body.

8. The umbilical arterial catheterization device of claim 4, wherein said fastener comprises a field of one of a hook-type fastener and a loop-type fastener of a hook-and-loop fastener system, and wherein said body comprises a respective field of another one of the hook-type fastener and the loop-type fastener.

9. The umbilical arterial catheterization device of claim 1, wherein said tip of said hook defines a sharp point.

10. The umbilical arterial catheterization device of claim 1, wherein said hook defines a loop providing a mounting point for attachment of said hook to said catch.

11. The umbilical arterial catheterization device of claim 1, wherein said catch comprises a second fastener, said second fastener being operable to secure said catch to said brace.

12. The umbilical arterial catheterization device of claim 11, wherein said second fastener comprises a field of one of a hook-type fastener and a loop-type fastener.

13. The umbilical arterial catheterization device of claim 1, further comprising:
    a lighting element supported on said brace.

14. The umbilical arterial catheterization device of claim 13, wherein said lighting element comprises a light source.

15. The umbilical arterial catheterization device of claim 14, wherein said lighting element comprises a light pipe for transmitting light emitted from a remotely-located light source.

16. The umbilical arterial catheterization device of claim 14, wherein said brace defines a recess open to a surface of said body and dimensioned to receive said lighting element, wherein said lighting element is disposed within said recess.

17. An umbilical arterial catheterization device configured for catheterization of an artery of a human's umbilical cord, the umbilical arterial catheterization device comprising:
    a brace comprising a body adapted to support and stabilize a free end of the umbilical cord, and a fastener operable to secure the body in an operative position for stably supporting and stabilizing the free end of the umbilical cord; and
    a dilator comprising:
        a hook having a tip dimensioned for receipt within the artery of the umbilical cord and operable to dilate a lumen of the artery; and a catch joined to said hook and operable to fix said dilator to said brace;

whereby said hook of said catch may be positioned within a lumen of the artery of the umbilical cord to dilate said artery while said brace is supporting and stabilizing the free end of the umbilical cord, and said catch may be secured to said brace in a desired position relative to said brace to maintain the artery in a dilated position.

18. An umbilical arterial catheterization device configured for catheterization of an artery of a human's umbilical cord, the umbilical arterial catheterization device comprising:

a brace comprising a body adapted to support a free end of the umbilical cord, and a fastener operable to secure the body in an operative position in which the free end of the umbilical cord is supported and stabilized; and a dilator comprising:
   a hook having a tip operable to dilate the artery; and
   a catch joined to said hook and supporting a second fastener operable to fix said dilator to said brace while said hook is dilating the lumen of the artery, to maintain the artery in a dilated position.

* * * * *